US00PP08738P

United States Patent [19]

van Andel

[11] Patent Number: Plant 8,738

[45] Date of Patent: May 17, 1994

[54] ALSTROEMERIA NAMED STARHAP

[75] Inventor: Jacob van Andel, Aalsmeer, Netherlands

[73] Assignee: Van Staaveren B.V., Aalsmeer, Netherlands

[21] Appl. No.: 25,580

[22] Filed: Mar. 3, 1993

[51] Int. Cl.[5] ..... A01H 5/00

[52] U.S. Cl. ..... Plt./87.1

[58] Field of Search ..... Plt. 87.1

*Primary Examiner*—James R. Feyrer

*Attorney, Agent, or Firm*—Tilton, Fallon, Lungmus & Chestnut

[57] ABSTRACT

A new and distinctive Alstroemeria cultivar particularly distinguished by its profuse and recurrent production of very large flowers, having six petals arranged in two concentric circles of three petals per flower. The outer petal being white and slightly tinted with a shade of red-purple with a marigold orange base, each of these outer petals having a few chrysanthemum crimson stripes. The inner petals are also white and are red-purple and lemon yellow with a lemon yellow base, each of these inner petals having a few Chrysanthemum crimson stripes.

1 Drawing Sheet

BACKGROUND OF THE NEW PLANT

This Alstroemeria cultivar originated as a spontaneous mutant of the hybrid parent Staverpi produced in my nursery at Aalsmeer, The Netherlands, plant, hereinafter identified, was discovered as an attractive off-type of various Alstroemeria varieties maintained at my nursery for breeding purposes. This particular sport was discovered as an attractive off-type because of its distinctive flower coloration and shape of the petal and its recurrent and profuse growth habit. The new Alstroemeria cultivar most closely resembles Staverpi. Staverpi is characterized by the venetian pink coloration of the outer tier of flower petals and the general buttercup yellow coloration of the inner petals which are particularly characterized by short brown pencil stripes which appear in longitudinal rows extending from end to end of these petals. The outer petals of the claimed cultivar are white with a slight tint of red-purple with a marigold orange base. Each of the outer petals has a few chrysanthemum crimson stripes. The inner petals are also white with a slight tint of red-purple and lemon yellow with a lemon yellow base. Like the outer petals, each of the inner petals has a few chrysanthemum stripes. Staverpi has six stamens, one opposite each petal. The anthers of Staverpi are green-yellow in color. The filaments, styles and stigmas of Staverpi are all salmon pink in color. The claimed cultivar also has six stamens, which are clustered around the style. The anthers of the claimed cultivar are grey-green in color. In addition, the color of the filaments, styles and stigmas of Starhap are all orange. This selected sport was propagated by me at Aalsmeer, The Netherlands, by dividing root stock with very satisfactory results and thereafter this selected plant was propagated through several successive generations in the same manner which demonstrated conclusively that the novel characteristics of the originally selected sport would be maintained from generation to generation and its homogeneity would be firmly established.

DESCRIPTION OF THE DRAWING

My new Alstroemeria plant is illustrated by the accompanying photographic drawing which, in full color, shows the form and coloration of the flowers as they appear with relatively close spacing at the upper end portion of the flowering stem of the plant. The colors shown are as nearly true to these herein specified as is reasonably possible to obtain by conventional photographic procedures.

DESCRIPTION OF THE NEW PLANT

The following is a detailed description of my new Alstroemeria plant as observed from plants grown under greenhouse conditions in Aalsmeer, The Netherlands, with the stated flower colors being according to The R.H.S. Colour Chart of The Royal Horticultural Society of London, England.

THE PLANT

Origin: Sport (spontaneous mutant).

Parentage: Staverpi (U.S. Plant Pat. No. 7,925). The parent plant is so identified in my business records of my nursery maintained at the offices in Aalsmeer, The Netherlands. The aforementioned sport are also recorded therein.

Classification:

*Botanic.*—Alstroemeria sport.

*Commercial.*—Alstroemeria sport.

Form: An upright bush.

Height: About 150–200 cm.

Growth rate: Flowering in about 3–4 months following the first planting.

Main stem length: 150–200 cm.

Strength: Strong.

Branching character: The main stem has an umbel in which 4–6 branches (peduncles) are grouped. At the end of the peduncle a flower is situated on a pedicel. Above the peduncle additional pedicels may occur. The number of flowers per branch is 2–3.

Growth: Vigorous.

Foliage:

*Quantity.*—Abundant.

*Number of leaves.*—30–40.

*Size and shape of leaf.*—The leaf is elliptical shaped, about 12–16 cm in length and about 2–3 cm in width.

*Margin type.*—Entire.

*Texture.*—Smooth.

*Color.*—Upper side — 137A. Under side — 137C.

Rhizomes: Yes.

*Color.*—RHS 155D.

*Size.*—10–20 cm.

THE BUD

Size:

*Diameter.*—1–2 cm.

*Length.*—4 cm.

Shape: Pear-shaped.

Rate of opening: Bud to flower in about 3–5 days.

Color of petals: The color of the petals of the claimed plant are white slightly tinted with a pastel shade of red-purple and this color effect is believed to have not been previously available in flowers of this market class.

Slitting: No.

THE FLOWER

Blooming habit: Recurrent and profuse — Spring and Fall.

Size of bloom: Very large.

*Diameter.*—7 cm.

*Depth.*—6 cm.

Borne: Singly.

Shape: When bloom first opens and when it matures the blooms are cup shaped.

Petalage:

*Numbers of petals.*—Six.

*Arrangement.*—Two concentric circles of three petals.

*Texture.*—Soft.

*Form.*—The two outer, lateral petals and the top petal are lobed at the apex. The three inner petals are substantially obovate.

*Margin type.*—Very finely dentate.

*Apex.*—Pointed.

*Appearance.*—Velvety.

*Remain on stem.*—Two weeks.

*Color.*—Outer petals Body: RHS 69A. Base:RHS 28C. Reverse Side: RHS 69A. Stripes: 1–5. Color: RHS 185A. Inside petals Body:RHS 69A/13A. Base:RHS 13A. Reverse side RHS 69A/13A. Stripes: 50–70. Color: RHS 185A.

Discoloration after full bloom: Slightly.

Persistence: The petals of matured flowers do not hang on and dry.

Fragrance: None.

Lasting quality:

*On the plant.*—About 3 weeks.

*As a cut flower.*—About 2 weeks.

Flower stem:

*Length.*—About 7–10 cm.

*Character.*—Upright and strong.

*Color.*—RHS 137A.

THE REPRODUCTIVE ORGANS

Stamens:

*Number.*—About six.

*Arrangement.*—Clustered around the style.

*Anthers.*—size: 8–10 mm. Color: RHS 194A.

*Filaments.*—Length: About 5 cm. Color: RHS 29C.

*Pollen.*—Color: RHS 4B.

Pistils:

*Number.*—One.

*Styles.*—Length about 4–5 cm (RHS 29C).

*Stigmas.*—RHS 29C.

Fruit:

*Fertile.*—No.

*Shape.*—Round.

I claim:

1. A new and distinctive Alstroemeria plant, substantially as herein shown and described.

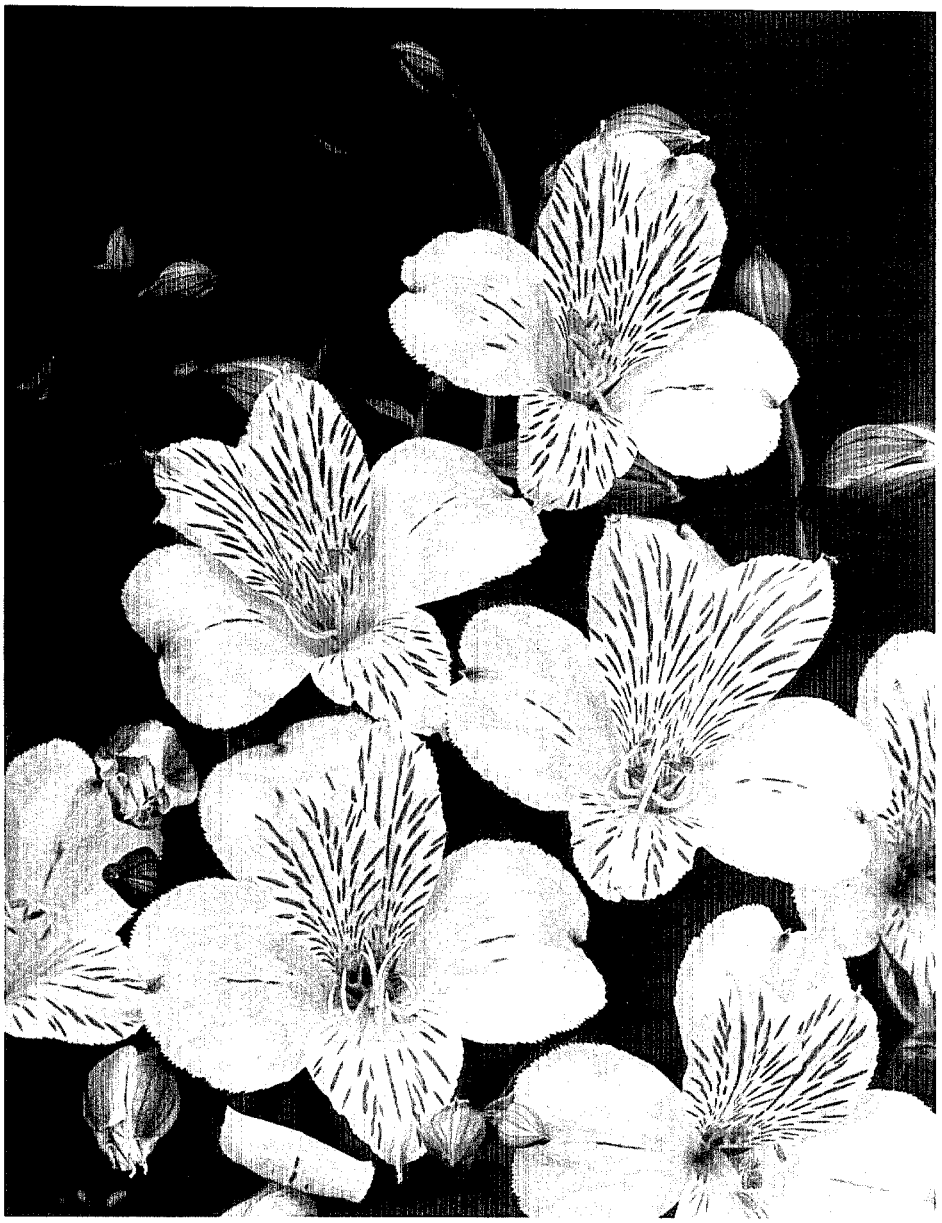

* * * * *